United States Patent
Schatzberg et al.

(12) 
(10) Patent No.: US 6,369,046 B1
(45) Date of Patent: Apr. 9, 2002

(54) METHODS FOR TREATING DEMENTIA

(75) Inventors: Alan F. Schatzberg, Los Altos; Joseph K. Belanoff, Woodside, both of CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 09/246,780

(22) Filed: Feb. 4, 1999

Related U.S. Application Data

(60) Provisional application No. 60/085,703, filed on May 15, 1998.

(51) Int. Cl.⁷ .......................... A61K 31/59; A61K 31/56
(52) U.S. Cl. ....................................... 514/167; 514/169
(58) Field of Search .................................. 514/167, 169

(56) References Cited

U.S. PATENT DOCUMENTS

| | | | | |
|---|---|---|---|---|
| 4,386,085 A | * | 5/1983 | Teutsch et al. | ............. 514/179 |
| 5,939,407 A | * | 8/1999 | Landfield | .................... 514/167 |

FOREIGN PATENT DOCUMENTS

| | | |
|---|---|---|
| EP | 0763541 A1 | 3/1997 |
| WO | WO 93/22685 | 11/1993 |
| WO | WO 94/08588 | 4/1994 |
| WO | WO 97/37664 | 10/1997 |

OTHER PUBLICATIONS

Drug Topics (Dec. 8, 1997) pp. 30—Aids Weekly Plus (Jul. 8, 1996).*
Aisen (1998) *Drugs & Aging* 12: 1–6.
Aisen (1997) *Gerontology* 43: 143–149.
Aisen (1996) *Mol. & Chem. Neruropathol.* 28: 83–88.
Asthana (1996) *Clin. Pharmacol. Ther.* 60: 276–282.
Behl et al. (1997) *Eur. J. Neurosci.* 9(5):912–920.
Bertagna (1984) *J. Clin. Endocrinol. Metab.* 59: 25–28.
Birge et al. (1996) *J. of the Am. Geriatics Soc.* 44(7): 865–870.
Brodaty (1997) *Med. J. Aust.* 167: 447–452.
Cadepond (1997) *Annu. rev. Med.* 48: 129–156.
deLeon (1997) *Int. Psychogeriatr.* 9(Suppl 1): 183–190.
Lupien et al. (May 1994) *Journal of Neuroscience* 14(5): 2893–2903.
Maeda et al. (1991) *Neurobiol. of Aging* 12: 161–163.
Sapolsky (1994) *Ann. NY Acad. Sci.* 746: 294–304.
Silva (1997) *Annu. Rev. Genet.* 31: 527–546.
Talmi et al (1996) *Neurobiology of Aging* 17(1): 9–14.
Tuor (1997) *Neuroscience and Biobehavioral Reviews* 21(2): 175–179.

* cited by examiner

*Primary Examiner*—Theodore J. Criares
(74) *Attorney, Agent, or Firm*—Bret E. Field; Bozicevic, Field & Francis LLP

(57) ABSTRACT

This invention generally pertains to the field of psychiatry. In particular, this invention pertains to the discovery that agents which inhibit the binding of cortisol to its receptors can be used in methods for treating dementia. Mifepristone, a potent glucocorticoid receptor antagonist, can be used in these methods. The invention also provides a kit for treating dementa in a human including a glucoccrticoid receptor antagonist and instructional material teaching the indications, dosage and schedule of administration of the glucocoticoid receptor antagonist.

20 Claims, No Drawings

METHODS FOR TREATING DEMENTIA

CROSS REFERENCE TO RELATED APPLICATIONS

The present application is a PCT Application of U.S. Provisional Application Ser. No. 60/085,703, filed May 15, 1998. The aforementioned application is explicitly incorporated herein by reference in its entirety and for all purposes.

FIELD OF THE INVENTION

This invention generally pertains to the field of psychiatry. In particular, this invention pertains to the discovery that agents which inhibit the binding of cortisol to its receptor can be used in methods of treating dementia.

BACKGROUND OF THE INVENTION

Dementia is loss of one's ability to think and remember. This condition afflicts many thousands of individuals, especially the elderly, and is becoming more common as our population ages. Typically, this loss of cognitive skills and memory is slow and progressive, taking many months or years. To date, there are no effective treatments which can stop, slow or reverse this process.

What causes dementia is controversial, resulting in many different and contrasting proposed theories of causation and methods of treatment. While dementia is commonly associated with Alzheimer's disease and multi-infarct, or vascular, dementia, it is also seen with a variety of other conditions. One generally agreed upon theory proposes that the death or injury of brain neurons, especially those in the hippocampus, leads to dementia. Dementia has also been associated with increased levels of cortisol. There is conflicting evidence as to whether this hypercortisolemia causes the brain damage or is the result of it. For example, not all conditions characterized by hypercortisolemia, such as Cushing's syndrome, are associated with dementia. One group proposed that brain damage may hyperactivate the cortisol regulatory system, resulting in hypercortisolemia. They suggested that elevated cortisol might be a biological marker of dementia and may have a value in diagnosis of dementia. They also suggested that this activation relates generally to cognitive decline itself, not to an etiology of dementia (Maeda (1991) Neurobiol Aging 12:161–163). Another theory proposes that increased levels of cortisol is neurotoxic, particularly in the hippocampus, a brain structure that is thought to be central to the processing and temporary storage of complex information and memory (Sapolsky (1994) Ann. NY Acad. Sci. 746:294–304); Silva (1997) Annu. Rev. Genet. 31:527–546). Hippocampal atrophy has been proposed to be a predictor of future Alzheimer's disease (de Leon (1997) Int. Psychogeriatr. 9 Suppl 1:183–190).

Yet another theory is exactly opposite our invention's. We propose that inhibition of cortisol activity (using receptor antagonists) will prevent dementia-inducing brain damage. In direct contrast, the alternative theory proposes that brain damage leading to dementia is caused by inflammation, such as that seen in autoimmunity. On this basis, it proposes that Alzheimer's disease is an autoimmune reaction directed against pathological brain tissue (e.g., senile plaques containing dystrophic neurites, Tau protein and condensed beta amyloid deposits; Gasiorowski (1997) Med. Hypotheses 49:319–326; Hull (1996) Neurobiol. Aging. 17:795–800). Thus, on the premise that it is a neurodegenerative disease mediated by inflammation, Alzheimer's disease is being treated by immunosuppression with synthetic cortisols. Ongoing clinical studies are using prednisone, a synthetic cortisol (agonist) (Aisen (1998) Drugs Aging 12:1–6; Aisen (1997) Gerontology 43:143–149; Aisen (1996) Mol. Chem. Neuropathol. 28:83–88). Other anti-inflammatory drugs (e.g., hydroxychloroquine and colchicine) are also undergoing clinical trials as treatments for Alzheimer's disease (Aisen (1998) supra).

To add to the confusion in the field, several additional theories and methods of treating dementia and Alzheimer's disease are being pursued. One believes that dementia is caused by death of cells which produce a memory-inducing neurotransmitter (forebrain cholinergic neurons). Thus, Alzheimer's disease is also being treated using cholinergic agonists in an effort to improve memory (Asthana (1996) Clin. Pharmacol Ther. 60:76–282). Another group proposes using estrogen to promote the growth of the memory-inducing neurons. Yet another theory to treat dementia proposes using Vitamin E (alpha-tocopherol), as it slows nerve cell death. Nerve growth factors have been proposed for the same reason. Calcium blockers (e.g., nimodipine) have also been evaluated as a treatment for Alzheimer's disease on the basis that blocking the increase in intracellular free calcium may retard the process of neuronal death and slow the progression of the disease (Brodaty (1997) Med. J. Aust. 167:447–449).

Thus, it is clear that to date there is no consensus as to the etiology or treatment of dementia. Before this invention, there was no effective treatment to treat dementia or to diminish the rate of cognitive decline in diseases such as Alzheimer's disease or multi-infarct dementia. Thus, there exists a great need for an effective and safe treatment for dementia, especially one that can decrease the rate and severity of the cognitive decline. The present invention fulfills these and other needs.

SUMMARY OF THE INVENTION

The invention provides a method of treating dementia in an individual diagnosed as having symptoms of dementia by administration of an amount of a glucocorticoid receptor antagonist effective to treat the dementia. In one embodiment, the glucocorticoid receptor antagonist is administered when the individual scores less than 30 on the Folstein Mini Mental Status Exam. In another embodiment, the glucocorticoid receptor antagonist is administered when the individual is diagnosed with early in the course of Alzheimer's disease, as indicated by a score of between about 21 and 29 on the Folstein Mini Mental Status Exam. The dementia can be associated with a condition selected from the group consisting of Alzheimer's disease and multi-infarct dementia. The dementia can be associated with Alzheimer's disease wherein the dementia is accompanied by absence of the apolipoprotein E4 allele or lack of expression of apolipoprotein E4.

In one embodiment, the invention's method of treating dementia uses a glucocorticoid receptor antagonist comprising a steroidal skeleton with at least one phenyl-containing moiety in the 11-beta position of the steroidal skeleton. The phenyl-containing moiety in the 11-beta position of the steroidal skeleton can be a dimethylaminophenyl moiety. In alternative embodiments, the glucocorticoid receptor antagonist comprises mifepristone, or, the glucocorticoid receptor antagonist is selected from the group consisting of RU009 and RU044.

In other embodiments, the glucocorticoid receptor antagonist is administered in a daily amount of between about 0.5 to about 20 mg per kilogram of body weight per day; between about 1 to about 10 mg per kilogram of body weight per day; or between about 1 to about 4 mg per kilogram of body weight per day. The administration can be once per day. In alternative embodiments, the mode of glucocorticoid receptor antagonist administration is oral, or by a transdermal application, by a nebulized suspension, or by an aerosol spray.

The invention also provides a kit for the treatment of dementia in a human, the kit comprising a glucocorticoid receptor antagonist; and, an instructional material teaching the indications, dosage and schedule of administration of the glucocorticoid receptor antagonist. In alternative embodiments, the instructional material indicates that the glucocorticoid receptor antagonist can be administered in a daily amount of about 0.5 to about 20 mg per kilogram of body weight per day, of about 1 to about 10 mg per kilogram of body weight per day, or about 1 to about 4 mg per kilogram of body weight per day. The instructional material can indicate that corticol contributes to the rate of cognitive decline in patients with dementia, and that the glucocorticoid receptor antagonist can be used to treat dementia. The kit's instructional material can further indicate that the glucocorticoid receptor antagonist can be used for the treatment of early in the course of Alzheimer's disease in patients who do not have the apolipoprotein E4 allele. In one embodiment, the glucocorticoid receptor antagonist in the kit is mifepristone. The mifepristone can in tablet form.

A further understanding of the nature and advantages of the present invention is realized by reference to the remaining portions of the specification, the figures and claims.

All publications, patents and patent applications cited herein are hereby expressly incorporated by reference for all purposes.

DEFINITIONS

The term "treating" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being; or, in some situations, preventing the onset of dementia. The treatment or amelioration of symptoms can be based on objective or subjective parameters; including the results of a physical examination and/or a psychiatric evaluation. For example, the methods of the invention successfully treat a patient's dementia by slowing the rate of or extent of cognitive decline.

The term "cortisol" refers to a family of compositions also referred to hydrocortisone, and any synthetic or natural analogues thereof.

The term "dementia" refers to a psychiatric condition in its broadest sense, as defined in American Psychiatric Association: *Diagnostic and Statistical Manual of Mental Disorders,* Fourth Edition, Washington, D.C., 1994 ("DSM-IV"). The DSM-IV defines "dementia" as characterized by multiple cognitive deficits that include impairments in memory and lists various dementias according to presumed etiology. The DSM-IV sets forth a generally accepted standard for such diagnosing, categorizing and treating of dementia and associated psychiatric disorders, including Alzheimer's disease and multi-infarct dementia, as described below.

The term "early in the course of Alzheimer's disease" refers to Alzheimer's disease in its early stages, as can be objected measured by a test score of between about 21 and 29 on the Folstein Mini Mental Status Exam.

The term "Folstein Mini Mental Status Exam" refers to the Mini-Mental State Examination (MMSE), as described by Folstein (1975) "'Mini-mental state.' An objective and practical method for grading the cognitive state of patients for the clinician." *J. Psychiatr. Res.* 12:189–198. The MMSE is one of many tests which can be used to objectively assess the treatment or amelioration of a dementia, i.e., an abatement, remission, diminishing of symptoms, slowing in the rate of degeneration or decline, delay or prevention of onset, or an improvement in a patient's cognitive well-being.

The term "glucocorticoid receptor antagonist" refers to any composition or compound which partially or completely inhibits (antagonizes) the binding of a glucocorticoid receptor (GR) agonist, such as cortisol, or cortisol analogs, synthetic or natural, to a GR. A "glucocorticoid receptor antagonist" also refers to any composition or compound which inhibits any biological response associated with the binding of a GR to an agonist.

The term "glucocorticoid receptor" ("GR") refers to a family of intracellular receptors also referred to as the cortisol receptor, which specifically bind to cortisol and/or cortisol analogs. The term includes isoforms of GR, recombinant GR and mutated GR.

The term "mifepristone" refers to a family of compositions also referred to as RU486, or RU38.486, or 17-beta-hydroxy-11-beta-(4-dimethyl-aminophenyl)-17-alpha-(1-propynyl)-estra-4,9-dien-3-one), or 11-beta-(4dimethylaminophenyl)-17-beta-hydroxy-17-alpha-(1-propynyl)-estra-4,9-dien-3-one), or analogs thereof, which bind to the GR, typically with high affinity, and inhibit the biological effects initiated/ mediated by the binding of any cortisol or cortisol analogue to a GR receptor. Chemical names for RU-486 vary; for example, RU486 has also been termed: 11B-[p-(Dimethylamino)phenyl]-17B-hydroxy-17-(1-propynyl)-estra-4,9-dien-3-one; 11B-(4-dimethyl-aminophenyl)-17B-hydroxy-17A-(prop-1-ynyl)-estra-4,9-dien-3-one; 17B-hydroxy- 11 B-(4-dimethylaminophenyl-1)-17A-(propynyl-1)-estra-4,9-diene-3-one; 17B-hydroxy-11B-(4-dimethylaminophenyl-1)-17A-(propynyl-1)-E; (11 B,17B)-11- [4-dimethylamino)-phenyl]-17-hydroxy-17-(1-propynyl)estra-4,9-dien-3-one; and 11B-[4-(N,N-dimethylamino) phenyl]-17A-(prop-1 -ynyl)-D-4,9-estradiene-17B-ol-3-one.

DETAILED DESCRIPTION OF THE INVENTION

This invention pertains to the surprising discovery that agents that can inhibit a biological response caused by an agonist-occupied glucocorticoid receptor (GR) are effective for treating dementia. In treating dementia, especially in the case of primary degenerative dementia of the Alzheimer type and multi-infarct dementia, the methods of the invention can slow the rate of or extent of cognitive decline. In one embodiment, the methods of the invention use agents that act as GR antagonists, blocking the interaction of cortisol with GR, to treat or ameliorate dementia. The methods of the invention are effective in slowing the rate of cognitive decline in a patient afflicted with dementia in patient's with either normal or increased levels of cortisol or other glucocorticoids, natural or synthetic.

Cortisol is a steroid and acts by binding to an intracellular, glucocorticoid receptor (GR). The biologic effects of cortisol, including pathologies or dysfunctions caused by hypercortisolemia, can be modulated and controlled at the GR level using receptor antagonists. Several different classes of agents are able to act as GR antagonists, i.e., to block the physiologic effects of GR-agonist binding (the natural agonist is cortisol). These antagonists include compositions which, by binding to GR, block the ability of an agonist to effectively bind to and/or activate the GR. One family of known GR antagonists, mifepristone and related compounds, are effective and potent anti-glucocorticoid agents in humans (Bertagna (1984) *J. Clin. Endocrinol. Metab.* 59:25). Mifepristone binds to the GR with high affinity, with a K of dissociation <$10^{-9}$ M (Cadepond (1997) *Annu. Rev. Med.* 48:129). Thus, in one embodiment of the invention, mifepristone and related compounds are used to treat dementia.

Dementia can be manifested as mental or psychological deficits that include impairments in memory and cognition. Thus, a variety of means of diagnosing dementia and assessing the success of treatment, i.e., the success and extent the dementia is treated by the methods of the invention, can be used, and a few exemplary means are set forth below. These means can include classical, subjective psychological evaluations and in addition to the objective tests describe below.

Dementia can also be manifested by physical, i.e., chemical or structural, changes. Thus, in addition to subjective and objective memory and cognition tests, a variety of laboratory procedures can be used. They include blood or histological analyses and brain functional and structural analyses. They can be used to diagose dementia and assess the efficacy of the methods of the invention. A few exemplary means to assess physical parameters are set forth below.

As the methods of the invention include use of any means to inhibit the biological effects of an agonist-bound GR, illustrative compounds and compositions which can be used to treat dementia are also set forth. Routine procedures that can be used to identify further compounds and compositions able to block the biological response caused by a GR-agonist interaction for use in practicing the methods of the invention are also described. As the invention provides for administering these compounds and compositions as pharmaceuticals, routine means to determine GR antagonist drug regimens and formulations to practice the methods of the invention are set forth below.

1. DIAGNOSING AND ASSESSING CONDITIONS AND ILLNESSES INVOLVING DEMENTIA

Dementia is typically characterized by multiple cognitive deficits that include impairments in memory. Dementia can be associated with a syndrome or as an element of a variety of disease processes. There are various means to diagnose the onset of dementia, these various forms or degrees of dementia, and to assess the success of treatment using the methods of the invention. These means are particularly useful for assessing the efficacy of the methods of the invention in decreasing or diminishing the rate of cognitive decline in a patient with a chronic disease, such as Alzheimer's disease or multiple infarct dementia. These means include classical psychological evaluations in addition to the various laboratory procedures described herein. Such means are well-described in the scientific and patent literature, and some illustrative examples are provided below.

a. Assessing and diagnosing dementia

Administration of the methods of the invention as soon as any sign or symptom of dementia is detected is important because the rate of cognitive deterioration can be rapid and, typically, the process of dementia cannot be reversed or halted, but only slowed or diminished. For example, in the case of Alzheimer's disease, the methods of the invention are practiced early in the course of (in the early stages of) the condition, and most preferably, at the first sign of the disease. This is especially critical in the case of early-onset Alzheimer's disease where the rate of cognitive decline is relatively rapid. In the case of an injury or poisoning, if it is reasonably expected that some degree of dementia may be a sequelae, the methods of the invention can be used prophylactically. Another scenario in which the methods of the invention would be applied prophylactically is where a patient is diagnosed as having a stroke (cerebral infarction) and concurrent cerebral atherosclerosis or hippocampal structural brain damage.

The dementia treated in the methods of the invention encompasses abroad range of mental conditions and symptoms, as broadly described in the DSM-IV, as defined above. While the practitioner can use any set of prescribed or empirical criteria to diagnose the presence of dementia as an indication to practice the methods of the invention, some illustrative diagnostic guidelines and examples of relevant symptoms and conditions are described below.

Dementia can be diagnosed by formal psychiatric assessment using subjective diagnosis or objective test criteria to determine whether an individual is afflicted with dementia or undergoing progressive cognitive decline. Subjective and objective criteria can be used to measure and assess the success of a particular GR antagonist, pharmaceutical formulation, dosage, treatment schedule or regimen. The features (symptoms) of and criteria for diagnosing dementia are described, e.g., in the DSM-IV, supra. While the practitioner can use any criteria or means to evaluate dementia to practice the methods of the invention, the DSM-IV sets forth a generally accepted standard for such diagnosing, categorizing and treating dementia and associated psychiatric disorders, including Alzheimer's disease and multi-infarct dementia. Several illustrative examples of such criteria utilized in the methods of the invention are set forth below.

The DSM-IV states that dementias typically associated with Alzheimer's disease (dementia of the Alzheimer's type), "vascular dementia" (also known as multi-infarct dementia), or "dementia due to general medical conditions," e.g., human immunodeficiency virus (HIV-1) disease, head trauma, Parkinson's disease, or Huntington's disease (further discussed, below). Dementias can also be "substance-induced persisting dementia," i.e., due to a drug of abuse, a medication, or toxin exposure, "dementia due to multiple etiologies," or a "dementia not otherwise specified" if the etiology is indeterminate.

Dementia can be diagnosed and evaluated using any of the many objective tests or criteria well-known and accepted in the fields of psychology or psychiatry. Objective tests can used to determine whether an individual is suffering from dementia and to measure and assess the success of a particular GR antagonist, pharmaceutical formulation, dosage, treatment schedule or regimen. For example, measuring changes in cognitive ability and memory aids in the diagnosis and treatment assessment of a patient with dementia. Any test known in the art can be used.

One objective test is the so-called Mini-Mental State Examination (MMSE), as described by Folstein (1975) "'Mini-mental state.' A practical method for grading the cognitive state of patients for the clinician." *J. Psychiatr. Res.* 12:189–198. The MMSE evaluates the the presence of global intellectual deterioration. See also Folstein (1997) "Differential diagnosis of dementia. The clinical process." *Psychiatr Clin North Am.* 20:45–57. The MMSE is a longrecognized means to evaluate the onset of dementia and the presence of global intellectual deterioration, as seen in Alzheimer's disease and multi-infart dementia. See, e.g., Kaufer (1998) *J. Neuropsychiatry Clin. Neurosci.* 10:55–63; Becker (1998) *Alzheimer Dis Assoc Disord.* 12:54–57; Ellis (1998) *Arch. Neurol.* 55:360–365; Magni (1996) Int. Psychogeriatr. 8:127–134; Monsch (1995) Acta Neurol. Scand. 92:145–150. The MMSE is scored from 1 to 30. The MMSE does not evaluate basic cognitive potential, as, for example, the so-called IQ test. Instead, it tests intellectual skills. A person of "normal" intellectual capabilities will score a "30" on the MMSE objective test (however, a person with a MMSE score of 30 could also score well below "normal" on an IQ test). Thus, a score of less than 30 indicates loss of a significant amount of intellectual capacity, a significant symptom of dementia (see DSM-IV criteria for diagnosis, below). Accordingly, the methods of the invention are appropriately administered when an individual scores less than 30 on the MMSE. As noted above, administration of the methods of the invention is important at the first sign of dementia, such as a score of less than 30 on the MMSE (or at the first indication or earliest sign of the disease using any objective or subjective criteria). In another embodiment, the methods of the invention are administered early in the course of Alzheimer's disease, as when the individual is diagnosed early in the couse of Alzheimer's disease as indicated by a score of between about 21 and 29 on the MMSE.

Another means to evaluate cognitive ability is the Alzheimer's Disease Assessment Scale (ADAS-Cog), or a variation termed the Standardized Alzheimer's Disease Assessment Scale (SADAS). It is commonly used as an efficacy measure in clinical drug trials of Alzheimer's disease and related disorders characterized by cognitive decline. SADAS and ADAS-Cog were not designed to diagnose Alzheimer's disease; they are useful in characterizing symptoms of dementia and are a relatively sensitive indicator of dementia progression. See, e.g., Doraiswamy (1997) *Neurology* 48:1511–1517; Standish (1996) *J. Am. Geriatr. Soc.* 44:712–716.

Evaluation of the presence and degree of cognitive decline can utilize a combination of subjective diagnosis and objective testing. For example, in one study, the degree of dementia in Alzheimer's disease patients was measured using the Alzheimer's Disease Assessment Scale-Cognitive Component, the Clinician Interview Based Impression, Mini-Mental State Examination, and the Caregiver-rated Clinical Global Impression of Change (Farlow (1998) *Neurology* 50:669–677). Another study used the Enhanced Cued Recall, Temporal Orientation, Verbal Fluency, and Clock Drawing tests to distinguish between patients with probable Alzheimer's disease and healthy control subjects (Solomon (1998) *Arch Neurol.* 55:349–355). Other tests, such as the Delirium Rating Scale (DRS) or Blessed Dementia Scale can also be used (Rockwood (1996) *J. Am. Geriatr. Soc.* 44:839–842).

When evaluating patients suspected of having multi-infarct disease-related dementia, combinations of tests can be given, including e.g., functional assessments (e.g., Functional Independence Measure, Barthel Index, Rankin Functional Scale), neurological assessments (e.g., Canadian Neurological Scale, National Institute of Healtb Stroke Scale), physical assessments (e.g., Stages of Motor Recovery, Clinical Outcome Variables Scale), and cognitive assessments (e.g., Stroke Unit Mental Status Examination, Mini Mental State Examination, Raven Matrices, Boston Naming Test), see, e.g., Hajek (1997) *Arch. Phys. Med. Rehabil.* 78:1331–1337; Wyller (1997) *Clin. Rehabil.* 11:139–145.

Physical and tissue structural and functional examinations can also be used adjunctively with subjective diagnostic criteria and objective testing as described above. For example, cerebral hemodynamics in patients with or suspected of having Alzheimer's disease or multi-infarct disease can be administered with the methods of the invention. Regional cerebral blood volume can be measured by, e.g., dynamic susceptibility contrast (DSC) MRI, positron emission tomography (PET), or single photon emission computed tomography (SPECT); see, e.g., Maas (1997) *J. Magn. Reson. Imaging* 7:215–219; Jagust (1996) *J. Neuroimaging* 6:156–160.

b. Diagnosing and Assessing Dementia of the Alzheimer's Type

Dementia associated with Alzheimer's disease is treated by the methods of the invention. As noted above, early diagnosis and treatment are critical, because dementia of the Alzheimer's type cannot be stopped or reversed and can progess rapidly, especially with early-onset Alzheimer's disease.

Alzheimer's disease has been subcategorized into familial and non-familial forms; and early-onset or sporatic forms. Even the early-onset form has been proposed to have two subtypes depending on the presence or absence of an apolipoprotein E e4 allele (Bronzova (1996) *J. Neurol.* 243:465–468). However, to practice the methods of the invention it is not important to ascertain which form of Alzheimer's disease a patient may or may not have. Early detection of the first signs of the disease, which is typically dementia, is the critical parameter so treatment with the methods of the invention can begin as soon as possible. It has been proposed that criteria other than dementia can be used in the early diagnosis of or prediction of acquiring Alzheimer's disease (Ohm (1997) *Mol. Psychiatry* 2:21–25). Thus, any physical, laboratory or genetic parameter can be used by the skilled artisan to determine that it is appropriate to treat an individual using the methods of the invention. Early diagnosis of dementia and early treatment will significantly decrease the rate and extent of cognitive decline and improve the patient's health and well-being.

As with dementia, Alzheimer's disease can be diagnosed with the aid of subjective diagnosis or objective tests. Other physical or genetic criteria can also be used to aid in the diagnosis and prognosis (adjunctive laboratory tests are discussed, below). For example, current candidate markers to diagnose early-onset familial Alzheimer's disease include mutations in the presenilin 1, presenilin 2, and amyloid precursor protein (APP) genes. Individuals with these mutations typically have increased levels of the amyloid Abeta42 peptide in plasma and decreased levels of APPs in cerebrospinal fluid. In late-onset and sporadic Alzheimer's disease, these measures are not useful, but detecting an apolipoprotein E e4 allele can add confidence to the clinical diagnosis. Among the other proposed molecular and biochemical markers for sporadic Alzheimer's disease, cerebrospinal fluid assays showing low levels of Abeta42 and high levels of tau come closest to fulfilling criteria for a useful biomarker (see *Neurobiol Aging* (1998) Mar; 19(2):109–116).

The DSM-IV states that diagnostic criteria for dementia of the Alzheimer's type includes a finding of multiple cognitive deficits as manifested by both memory impairment and one or more of the following cognitive disturbances: aphasia (language disturbance); apraxia (impaired ability to carry out motor activites despite intact motor function); agnosia (failure to recognize or identify objects despite intact sensory function); or, disturbance in executive functioning (i.e., planning, organizing, sequence, abstracting). Memory impairment is the impaired ability to learn new information or to recall previously learned information.

The onset of dementia of the Alzheimer's type is typically gradual. Onset involves continuing cognitive decline such that the memory impairment and aphasia, apraxia, agnosia, or disturbance in executive functioning each cause significant impairment in social or occupational functioning. A significant decline from a previous level of functioning must also be present. Because of the difficulty of obtaining direct pathological evidence of the presence of Alzheimer's disease, the diagnosis can be made only when other etiologies for the dementia have been ruled out. Specifically, the cognitive deficits are not due to other central nervous system (CNS) conditions that cause progressive deficits in memory or cognition. These may include, e.g., cerebrovascular disease, Parkinson's disease, Huntington's disease, subdural hematoma, normal-pressure hydrocephalus, or brain tumor. In diagnosing dementia of the Alzheimer's type, the cognitive deficits are also not due to systemic conditions that are known to cause dementia, e.g., hypothyroidism, vitamin $B_{12}$ deficiency, HIV infection, neurosyphilis, hypercalcemia, niacin deficiency, or folic acid deficiency. The cognitive deficits are also not due to the persisting effects of a substance or toxin, e.g., alcohol or pesticide. Delirium may be superimposed on a preexisting dementia of the Alzheimer's type, in which case the "with delirium" subtype should be diagnosed. Finally, the cognitive deficits are not better accounted for by another DSM-IV Axis I disorder (e.g., "major depressive disorder" or schizophrenia).

In addition to dementia, behavioral changes are also commonly seen in Alzheimer's patients, including psychosis, depression, anxiety, personality alterations, and neurovegetative changes. See, e.g., Engelborghs (1997) *Acta Neurol. Belg.* 97:67–84; Cummings (1996) *Neurology* 47:876–883; Samson (1996) *Eur. Neurol.* 36:103–106. Agitation is especially common and persistent in patients with Alzheimer disease (Devanand (1997) *Arch. Gen. Psychiatry* 54:257–263).

Dementia of the Alzheimer's type typically has associated laboratory findings. In the majority of cases, brain atrophy is present, with wider cortical sulci and larger cerebral ventricles than would be expected given the normal aging process. This can be determined by computed tomography (CT), magnetic resonance imaging (MRI), dynamic susceptibility contrast (DSC) MRI, positron emission tomography (PET), or single photon emission computed tomography (SPECT). Microscopic examination usually reveals histopathological changes, including senile plaques, neurofibrillary tangles, granulovascular degeneration, neuronal loss, astrocytic gliosis, and amyloid angiopathy. Lewy bodies are sometimes seen in the cortical neurons. See, e.g., Dickson (1996) *J. Neural Transm. Suppl.* 47:31–46; Mega (1997) *Neuroimage* 5:147–153.

Dementia of the Alzheimer's type typically has associated physical examination findings and general medical conditions. In the first years of illness, few motor and sensory signs are associated with dementia of the Alzheimer's Type. Later in the course, myoclonus and gait disorder may appear. Seizures occur in approximately 10% of individuals with the disorder. Culture and age features can also be associated with dementia. Late onset (after age 65 years) of dementia of the Alzheimer's type is much more common than early onset. Few cases develop before age 50 years. The disorder is slightly more common in females than in males. Between 2% and 4% of the population over age 65 years is estimated to have dementia of the Alzheimer's type. The prevalence increases with increasing age, particularly after age 75 years.

The course of dementia of the Alzheimer's type tends to be slowly progressive, with a loss of 3 to 4 points per year on a standard assessment instrument such as the MMSE, describe aboved. However, early diagnosis and treatment with the methods of the invention are still critical, because dementia of the Alzheimer's type cannot be stopped or reversed. Thus, in one embodiment of the invention, the glucocorticoid receptor antagonist is administered at the earliest sign of the disease, e.g., when the individual scores less than 30 on the MMSE. In another embodiment, the glucocorticoid receptor antagonist is administered when the patient is in the early stages of Alzheimer's disease as indicated by a score of between about 21 and 29 on the MMSE.

Various patterns of deficits are seen. A common pattern is an insidious onset, with early deficits in recent memory followed by the development of aphasia, apraxia, and agnosia after several years. Some individuals may show personality changes or increased irritability in the early stages. In the later stages of the disease, individuals may develop gait and motor disturbances and eventually become mute and bedridden. The average duration of the illness from onset of symptoms to death is 8 to 10 years.

Compared with the general population, first-degree biological relatives of individuals with dementia of the Alzheimer's type "with early onset," are more likely to develop the disorder. Late-onset cases may also have a genetic component. Dementia of the Alzheimer's type in some families has been show to be inherited as a dominant trait with linkage to several chromosomes, including chromosomes 21, 14, and 19. However, the proportion of cases that are related to specific inherited abnormalities is not known.

c. Diagnosing and Assessing Multi-Infarct Dementia (Vascular Dementia)

Dementia associated with multi-infarct dementia (also called ischemic vascular dementia or vascular dementia) is treated by the methods of the invention. Vascular dementia is considered to be the second most common cause of dementia after Alzheimer's disease (Lowe (1998) *Brain Pathol.* 8:403–406). Etiologically, vascular dementia has a presumed association with cerebral arteriosclerosis (Lechner (1998) *Neuroepidemiology* 17:10–13). For differential diagnosis, one study compared individuals with multi-infarct dementia to those with Alzheimer's disease and found patients were matched on the basis of age, dementia severity; years of education, and gender. The multi-infarct dementia patients had poorer verbal fluency, but better free recall, fewer recall intrusions, and better recognition memory than the Alzheimer's disease patients (Lafosse (1997) *Neuropsychology* 11:514–522). Another comparison of individuals with multi-infarct dementia to those with Alzheimer's disease found no group differences in those variables reflecting primary memory and dementia-related deficits in secondary memory; no group differences in face recognition and object recall, and an advantage of multi-infarct dementia patients compared with Alzheimer's disease patients in word recall (Hassing (1997) *Dement. Geriatr. Cogn. Disord.* 8:376–383). See, e.g., Erkinjuntti (1997) *Int. Psychogeriatr.* 9 Suppl 1:51–58; Konno (1997) *Drugs Aging* 11:361–373.

The DSM-IV states that the diagnostic criteria for vascular dementia includes a finding of multiple cognitive deficits as manifested by both memory impairment and one or more cognitive disturbances, including aphasia, apraxia, agnosia, or disturbance in executive functioning. In vascular dementia, cognitive deficits are such that the memory impairment and aphasia, apraxia, agnosia, or disturbance in executive functioning each cause significant impairment in social or occupational functioning and represent a significant decline from a previous level of functioning.

To diagnose vascular dementia, there must also be evidence of cerebrovascular disease, i.e. focal neurological signs and symptoms or laboratory evidence, that is judged to be etiologically related to the dementia. The focal neurological signs and symptoms include extensor plantar response, pseudobulbar palsy, gait abnormalities, exaggeration of deep tendon reflexes, or weakness of an extremity, or laboratory evidence indicative of cerebrovascular disease. Computer tomography (CT) of the head, magnetic resonance imaging (MRI), dynamic susceptibility contrast (DSC) MRI, positron emission tomography (PET), or single photon emission computed tomography (SPECT) can demonstrate multiple vascular lesions of the cerebral cortex and subcortical structures. Vascular dementia is not diagnosed if the symptoms occur exclusively during delirium. However, delirium may be superimposed on a preexisting vascular dementia, in which case the subtype "with delirium" should be diagnosed.

The extent of CNS lesions detected by CT, MRI, PET, and the like, in vascular dementia typically exceeds the extent of changes detected in the brains of healthy elderly persons (e.g., periventricular and white matter hyperintensities noted on MRI scans). Lesions often appear in both white matter and gray matter structures, including subcortical regions and nuclei. Evidence of old infarctions (e.g. focal atrophy) may be detected, as well as findings of more recent disease. EEG findings may reflect focal lesions in the brain. In addition, there may be laboratory evidence of associated cardiac and systemic vascular conditions (e.g. ECG abnormalities, evidence of renal failure).

Associated physical examination findings and general medical conditions-found in individuals with vascular dementia include common neurological signs (e.g., abnormal reflexes, weakness of an extremity, gait disturbance, discussed above). There is often evidence of longstanding arterial hypertension (e.g., funduscopic abnormalities, enlarged heart), valvular heart disease (e.g., abnormal heart sounds), or extracranial vascular disease that may be sources of cerebral emboli. A single stroke may cause a relatively circumscribed change in mental state (e.g., an aphasia following damage to the left hemisphere, or an amnestic disorder from infarction in the distribution of the posterior cerebral arteries), but generally does not cause vascular dementia, which typically results from the occurrence of multiple strokes, usually at different times.

The onset of vascular dementia is typically abrupt, followed by a stepwise and fluctuating course that is characterized by rapid changes in functioning rather than slow progression. The course, however, may be highly variable, and an insidious onset with gradual decline is also encountered. Usually the pattern of deficits is "patchy," depending on which regions of the brain have been destroyed. Certain cognitive functions may be affected early, whereas others remain relatively unimpaired.

d. Diagnosing and Assessing Dementia Due to General Medical Conditions

Dementia associated with degenerative pathologies involving cognitive decline is treated by the methods of the invention. While the invention is not limited by any specific mechanism of action, the administered GR antagonists can be offsetting the dementia-inducing effects of cortisol. Cortisol has been speculated to exacerbate and accelerate the rate of intellectual deterioration and cognitive decline in an individual experiencing cognitive decline, as from, e.g., Alzheimer's disease, multi-infarct dementia, frontotemporal dementia, or other conditions, toxins or injury, as summarized in the DSM-IV. It is believed that the diseased or injured brain is predisposed to further injury, disease or toxic effects, such as those effected by cortisol or other glucocorticoids. In these pre-disposed patients, levels of cortisol that are considered within a "normal" range can accelerate or exacerbate the rate of cognitive decline. Thus, the methods of the invention are directed to the treatment of dementia in patients suffering from or predisposed to any form of dementia, including those due to toxins, drug side-effects, injuries, general medical conditions, frontotemporal dementia, and the like.

The dementia treated in the methods of the invention encompasses a broad range of mental conditions and symptoms, including those due to general medical conditions, as described in the DSM-IV, as discussed above. The DSM-IV states that in addition to findings of cognitive deficits and other impairments, there must be evidence from the history, physical examination or laboratory findings that a general medical condition is etiologially related to the dementia. Such general medical conditions include, e.g., infection with HIV-1, traumatic brain injury, Parkinson's disease, Huntington's disease, Pick's disease, Creutzfeldt-Jakob disease, normal-pressure hydorcephalus, brain tumor, subdural hematoma, endocrine conditions as hypothyroidism, hypercalcemia, hypoglycemia, nutritional conditions, as deficiencies of thiamine, niacin or vitamin $B_{12}$, infections, as neurosyphillis, cryptococcosis, derangements of renal or hepatic function, other neurological conditions, as multiple sclerosis, or rare storage diseases.

"Pick's disease" includes one group of frontotemporal dementias (FTD) composed of non-Alzheimer forms of dementia. They are characterized clinically by behavioral and personality change leading to apathy and mutism. One disorder is associated with a progressive atrophy of the frontal, anterior temporal and anterior parietal lobes of the brain with several types of underlying pathology. One type (frontal lobe degeneration) is characterized by a microvacuolar degeneration of the outer cortical laminae along with a mild and mainly subpial gliosis and a loss of nerve cells. Another type shows transcortical tissue cavitation and florid gliosis with neuronal degeneration characterized by the presence of tau and ubiquitin positive inclusion bodies and alpha beta-crystallin-positive ballooned neurones. Such changes have been termed "Pick-type histology," and form the basis for the modem definition of "Pick's disease." See, e.g. Mann (1998) *Brain Pathol.* 8:325–338.

Dementia can also be caused by substance intake, whether as a side effect of medication, an environmental poisoning or because of substance abuse. This form of dementia is classified by the DSM-IV as "substance-induced persisting dementia." This form of dementia can occur in association within take of alcohol, inhalants, hypnotics or anxiolytics. Medications reported to cause dementia include, e.g., anti-convulsants and intrathecal methotrexate (Femandez-Bouzas (1992) *J. Neurosurg. Sci.* 36:211–214). Toxins reported to cause dementia include, e.g., lead, mercury, carbon monoxide, organophosphates (e.g., insecticides), and industrial solvents (see, e.g., Lolin (1989) *Hum Toxicol.* 8:293–300).

2. GENERAL LABORATORY PROCEDURES

A number of general laboratory tests can be used to assist in the diagnosis, progress and prognosis of the patient with dementia, including monitoring of parameters such as blood cortisol, drug metabolism, brain structure and function and the like can be practiced with the methods of the invention.

These procedures can be helpful because all patients metabolize and react to drugs uniquely. In addition, such monitoring may be important because each GR antagonist has different pharmacokinetics. Different patients and disease conditions may require different dosage regimens and formulations. Such procedures and means to determine dosage regimens and formulations are well described in the scientific and patent literature. A few illustrative examples are set forth below.

a. Determining Blood Cortisol Levels

Varying levels of blood cortisol, especially high levels of cortisol, have been associated with dementia and the rate and degree of cognitive decline. For example, among individuals with early-stage Alzheimer's disease who do not have apolipoprotein E4 alleles, a higher baseline cortisol measure is associated with a significantly greater rate of decline in cognitive function. Thus, monitoring blood cortisol and determining baseline cortisol levels can be a useful laboratory test to aid in the diagnosis, treatment and prognosis of the patient. A wide variety of laboratory tests exist that can be used to determine whether an individual is normal, hypo- or hypercortisolemic. Immunoassays such as radioimmunoassays are commonly used because they are accurate, easy to do and relatively cheap. Because levels of circulating cortisol is an indicator of adrenocortical function, a variety of stimulation and suppression tests, such as ACTH Stimulation, ACTH Reserve, dexamethasone suppression test (see, e.g., Greenwald (1986) Am. J Psychiatry 143:442–446), can also provide diagnostic, prognostic or other information to be used adjunctively in the methods of the invention.

One such assay available in kit form is the radioimmunoassay available as "Double Antibody Cortisol Kit™" (Diagnostic Products Corporation, Los Angeles, Calif., (1984) Acta Psychiatr. Scand. 70:239–247). This test is a competitive radioimmunoassay in which $^{125}$I-labeled cortisol competes with cortisol from an clinical sample for antibody sites. In this test, due to the specificity of the antibody and lack of any significant protein effect, serum and plasma samples require neither preextraction nor pre-dilution. This assay is described in further detail in Example 1, below.

b. Determining Blood/Urine Mifepristone Levels

Because a patient's metabolism, clearance rate, toxicity levels, etc. differs with variations in underlying primary or secondary disease conditions, drug history, age, general medical condition and the like, it may be necessary to measure blood and urine levels of GR antagonist. Means for such monitoring are well described in the scientific and patent literature. As in one embodiment of the invention mifepristone is administered to treat dementia, an illustrative example of determining blood and urine mifepristone levels is set forth in the Example below.

c. Other Laboratory Procedures

Because dementia can be associated with a variety of diseases, conditions, and drug effects, a number of additional laboratory tests can be used adjunctively in the methods of the invention to assist in diagnosis, treatment efficacy, prognosis, toxicity and the like. For example, as increased hypercortisolemia has also been associated with psychosis and depression, diagnosis and treatment assessment can be augmented by monitoring and measuring glucocorticoid-sensitive variables, including but limited to fasting blood sugar, blood sugar after oral glucose administration, plasma concentrations thyroid stimulating hormone (TSH), corticosteroid-binding globulin, luteinizing hormone (LH), testosterone-estradiol-binding globulin, and/or total and free testosterone. Laboratory tests monitoring and measuring GR antagonist metabolite generation, plasma concentrations and clearance rates, including urine concentration of antagonist and metabolites, may also be useful in practicing the methods of the invention. For example, mifepristone has two hydrophilic, N-monomethylated and N-dimethylated, metabolites. Plasma and urine concentrations of these metabolites (in addition to RU486) can be determined using, for example, thin layer chromatography, as described in Kawai (1987) Pharmacol. and Experimental Therapeutics 241:401–406.

3. GLUCOCORTICOID RECEPTOR ANTAGONISTS TO TREAT DEMENTIA

The invention provides for methods of treating dementia utilizing any composition or compound that can block a biological response associated with the binding of cortisol or a cortisol analogue to a GR. Antagonists of GR activity utilized in the methods of the invention are well described in the scientific and patent literature. A few illustrative examples are set forth below.

a. Steroidal Anti-Glucocorticoids as GR Antagonists.

Steroidal glucocorticoid antagonists are administered for the treatment of dementia in various embodiments of the invention. Steroidal antiglucocorticoids can be obtained by modification of the basic structure of glucocorticoid agonists, i.e., varied forms of the steroid backbone. The structure of cortisol can be modified in a variety of ways. The two most commonly known classes of structural modifications of the cortisol steroid backbone to create glucocorticoid antagonists include modifications of the 11-beta hydroxy group and modification of the 17-beta side chain (see, e.g., Lefebvre (1989) J. Steroid Biochem. 33:557–563).

i. Removal or Substitution of the 11-beta Hydroxy Group

Glucocorticoid agonists with modified steroidal backbones comprising removal or substitution of the 11-beta hydroxy group are administered in one embodiment of the invention. This class includes natural antiglucocorticoids, including cortexolone, progesterone and testosterone derivatives, and synthetic compositions, such as mifepristone (Lefebvre, et al. (1989) Ibid). Preferred embodiments of the invention include all 11-beta-aryl steroid backbone derivatives because these compounds are devoid of progesterone receptor (PR) binding activity (Agarwal (1987) FEBS 217:221–226). Another preferred embodiment comprises an 11-beta phenyl-aminodimethyl steroid backbone derivative, i.e., mifepristone, which is both an effective anti-glucocorticoid and anti-progesterone agent. These compositions act as reversibly-binding steroid receptor antagonists. For example, when bound to a 1-beta phenyl-aminodimethyl steroid, the steroid receptor is maintained in a conformation that cannot bind its natural ligand, such as cortisol in the case of GR (Cadepond (1997), supra).

Synthetic 11-beta phenyl-aminodimethyl steroids include mifepristone, also known as RU486, or 17-beta-hydrox-11-beta-(4-dimethyl-aminophenyl) 17-alpha-(1-propynyl)estra-4,9-dien-3-one). Mifepristone has been shown to be a powerful antagonist of both the progesterone and glucocorticoid (GR) receptors. Another 11-beta phenyl-aminodimethyl steroids shown to have GR antagonist effects includes RU009 (RU39.009), 11-beta-(4-dimethyl-aminoethoxyphenyl)- 1 7-alpha-(propynyl- 17 beta-hydroxy-4,9-estradien-3-one) (see Bocquel (1993) J. Steroid Biochem. Molec. Biol. 45:205–215). Another GR antagonist related to RU486 is RU044 (RU43.044) 17-beta-hydrox-17-alpha-19-(4-methyl-phenyl)-androsta-4,9(11)-dien-3-one) (Bocquel (1993) supra). See also Teutsch (1981) Steroids 38:651–665; U.S. Pat. Nos. 4,386,085 and 4,912,097.

One embodiment includes compositions containing the basic glucocorticoid steroid structure which are irreversible anti-glucocorticoids. Such compounds include alpha-ketomethanesulfonate derivatives of cortisol, including cortisol-21-mesylate (4-pregnene-11-beta, 17- alpha, 21-triol-3, 20-dione-21-methane-sulfonate and dexamethasone-21-mesylate (16-methyl-9 alpha-fluoro-1,4-pregnadiene-11 beta, 17-alpha, 21-triol-3, 20-dione-21-methane-sulfonate). See Simons (1986) *J. Steroid Biochem.* 24:25–32 (1986); Mercier (1986) *J. Steroid Biochem.* 25:11–20; U.S. Pat. No. 4,296,206.

ii. Modification of the 17-beta Side Chain Group

Steroidal antiglucocorticoids which can be obtained by various structural modifications of the 17-beta side chain are also used in the methods of the invention. This class includes synthetic antiglucocorticoids such as dexamethasone-oxetanone, various 17, 21-acetonide derivatives and 17-beta-carboxamide derivatives of dexamethasone (Lefebvre (1989) supra; Rousseau (1979) *Nature* 279:158–160).

iii. Other Steroid Backbone Modifications

GR antagonists used in the various embodiments of the invention include any steroid backbone modification which effects a biological response resulting from a GR-agonist interaction. Steroid backbone antagonists can be any natural or synthetic variation of cortisol, such as adrenal steroids missing the C-19 methyl group, such as 19-nordeoxycorticosterone and 19-norprogesterone (Wynne (1980) *Endocrinology* 107:1278–1280).

In general, the 11-beta side chain substituent, and particularly the size of that substituent, can play a key role in determining the extent of a steroid's antiglucocorticoid activity. Substitutions in the A ring of the steroid backbone can also be important. 17-hydroxypropenyl side chains generally decrease antiglucocorticoidal activity in comparison to 17-propinyl side chain containing compounds.

b. Non-Steroidal Anti-Glucocorticoids as Antagonists.

Non-steroidal glucocorticoid antagonists are also used in the methods of the invention to treat dementia. These include synthetic mimetics and analogs of proteins, including partially peptidic, pseudopeptidic and non-peptidic molecular entities. For example, oligomeric peptidomimetics useful in the invention include (alpha-beta-unsaturated) peptidosulfonamides, N-substituted glycine derivatives, oligo carbamates, oligo urea peptidomimetics, hydrazinopeptides, oligosulfones and the like (see, e.g., Amour (1994) *Int. J. Pept. Protein Res.* 43:297–304; de Bont (1996) *Bioorganic & Medicinal Chem.* 4:667–672). The creation and simultaneous screening of large libraries of synthetic molecules can be carried out using well-known techniques in combinatorial chemistry, for example, see van Breemen (1997) *Anal Chem* 69:2159–2164; Lam (1997) *Anticancer Drug Des* 12:145–167 (1997). Design of peptidomimetics specific for GR can be designed using computer programs in conjunction with combinatorial chemistry (combinatorial library) screening approaches (Murray (1995) *J. of Computer-Aided Molec. Design* 9:381–395); Bohm (1996) *J. of Computer-Aided Molec. Design* 10:265–272). Such "rational drug design" can help develop peptide isomerics and conformers including cycloisomers, retro-inverso isomers, retro isomers and the like (as discussed in Chorev (1995) *Tib Tech* 13:438–445).

c. Identifying Glucocorticoid Receptor Antagonists

Because any GR antagonist can be used for the treatment of dementia in the methods of the invention, in addition to the compounds and compositions described above, additional useful GR antagonists can be determined by the skilled artisan. A variety of such routine, well-known methods can be used and are described in the scientific and patent literature. They include in vitro and in vivo assays for the identification of additional GR antagonists. A few illustrative examples are described below.

One assay that can be used to identify a GR antagonist of the invention measures the effect of a putative GR antagonist on tyrosine amino-transferase activity in accordance with the method of Granner (1970) *Meth. Enzymol.* 15:633. This analysis is based on measurement of the activity of the liver enzyme tyrosine amino-transferase (TAT) in cultures of rat hepatoma cells (RHC). TAT catalyzes the first step in the metabolism of tyrosine and is induced by glucocorticoids (cortisol) both in liver and hepatoma cells. This activity is easily measured in cell extracts. TAT converts the amino-group of tyrosine to 2-oxoglutaric acid. P-hydroxyphenylpyruvate is also formed. It can be converted to the more stable p-hydroxybenzaldehyde in an alkaline solution and quantitated by absorbance at 331 nm. The putative GR antagonist is co-administered with cortisol to whole liver, in vivo or ex vivo, or hepatoma cells or cell extracts. A compound is identified as a GR antagonist when its administration decreases the amount of induced TAT activity, as compared to control (i.e., only cortisol or GR agonist added) (see also Shirwany (1986) "Glucocorticoid regulation of hepatic cytosolic glucocorticoid receptors in vivo and its relationship to induction of tyrosine aminotransferase," *Biochem. Biophys. Acta* 886:162–168).

Further illustrative of the many assays which can be used to identify compositions utilized in the methods of the invention, in addition to the TAT assay, are assays based on glucocorticoid activities in vivo. For example, assays that assess the ability of a putative GR antagonist to inhibit uptake of $^3$H-thymidine into DNA in cells which are stimulated by glucocorticoids can be used. Alternatively, the putative GR antagonist can complete with $^3$H-dexamethasone for binding to a hepatoma tissue culture GR (see, e.g., Choi (1992) "Enzyme induction and receptor-binding affinity of steroidal 20-carboxamides in rat hepatoma tissue culture cells," *Steroids* 57:313–318). As another example, the ability of a putative GR antagonist to block nuclear binding of $^3$H-dexamethasone-GR complex can be used (Alexandrova (1992) "Duration of antagonizing effect of RU486 on the agonist induction of tyrosine aminotransferase via glucocorticoid receptor," *J. Steroid Biochem. Mol. Biol.* 41:723–725). To further identify putative GR antagonists, kinetic assays able to discriminate between glucocorticoid agonists and antagonists by means of receptor-binding kinetics can also be used (as described in Jones (1982) *Biochem J.* 204:721–729).

In another illustrative example, the assay described by Daune (1977) *Molec. Pharm.* 13:948–955, and in U.S. Pat. No. 4,386,085, can be used to identify anti-glucocorticoid activity. Briefly, the thymocytes of surrenalectomized rats are incubated in nutritive medium containing dexamethasone with the test compound (the putative GR antagonist) at varying concentrations. $^3$H-uridine is added to the cell culture, which is further incubated, and the extent of incorporation of radiolabel into polynucleotide is measured. Glucocorticoid agonists decrease the amount of $^3$H-uridine incorporated. Thus, a GR antagonist will oppose this effect.

For additional compounds that can be utilized in the methods of the invention and methods of identifying and making such compounds, see U.S. Pat. Nos. 4,296,206 (see above); 4,386,085 (see above); 4,447,424; 4,477,445; 4,519, 946; 4,540,686; 4,547,493; 4,634,695; 4,634,696; 4,753, 932; 4,774,236; 4,808,710; 4,814,327; 4,829,060; 4,861, 763; 4,912,097; 4,921,638; 4,943,566; 4,954,490; 4,978, 657; 5,006,518; 5,043,332; 5,064,822; 5,073,548; 5,089, 488; 5,089,635; 5,093,507; 5,095,010; 5,095,129; 5,132, 299; 5,166,146; 5,166,199; 5,173,405; 5,276,023; 5,380, 839; 5,348,729; 5,426,102; 5,439,913; and 5,616,458; and WO 96/19458, which describes non-steroidal compounds which are high-affinity, highly selective modulators (antagonists) for steroid receptors, such as 6-substituted-1, 2-dihydro N-1 protected quinolines.

4. TREATMENT OF CONDITIONS AND ILLNESSES ASSOCIATED WITH DEMENTIA USING GLUCOCORTICOID RECEPTOR ANTAGONISTS

Antiglucocorticoids, such as mifepristone, are formulated as pharmaceuticals to be used in the methods of the invention to treat dementia. Any composition or compound that can block a biological response associated with the binding of cortisol or a cortisol analogue to a GR can be used as a pharmaceutical in the invention. Routine means to determine GR antagonist drug regimens and formulations to practice the methods of the invention are well described in the patent and scientific literature, and some illustrative examples are set forth below.

a. Glucocorticoid Receptor Antagonists as Pharmaceutical Compositions

The GR antagonists used in the methods of the invention can be administered by any means known in the art, e.g., parenterally, topically, orally, or by local administration, such as by aerosol or transdermally. The methods of the invention provide for prophylactic and/or therapeutic treatments. The GR antagonists as pharmaceutical formulations can be administered in a variety of unit dosage forms depending upon the condition or disease and the degree of dementia, the general medical condition of each patient, the resulting preferred method of administration and the like. Details on techniques for formulation and administration are well described in the scientific and patent literature, see, e.g., the latest edition of *Remington's Pharmaceutical Sciences,* Maack Publishing Co, Easton Pa. ("Remington's").

GR antagonist pharmaceutical formulations can be prepared according to any method known to the art for the manufacture of pharmaceuticals. Such drugs can contain sweetening agents, flavoring agents, coloring agents and preserving agents. Any GR antagonist formulation can be admixtured with nontoxic pharmaceutically acceptable excipients which are suitable for manufacture.

Pharmaceutical formulations for oral administration can be formulated using pharmaceutically acceptable carriers well known in the art in appropriate and suitable dosages. Such carriers enable the pharmaceutical formulations to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be obtained through combination of GR antagonist compounds with a solid excipient, optionally grinding a resulting mixture, and processing the mixture of granules, after adding suitable additional compounds, if desired, to obtain tablets or dragee cores. Suitable solid excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain GR antagonist mixed with a filler or binders such as lactose or starches, lubricants such as talc or magnesium stearate, and, optionally, stabilizers. In soft capsules, the GR antagonist compounds may be dissolved or suspended in suitable liquids, such as fatty oils, liquid paraffin, or liquid polyethylene glycol with or without stabilizers.

Aqueous suspensions of the invention contain a GR antagonist in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending a GR antagonist in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) *J. Pharmacol Exp. Ther.* 281:93–102. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

Dispersible powders and granules of the invention suitable for preparation of an aqueous suspension by the addition of water can be formulated from a GR antagonist in admixture with a dispersing, suspending and/or wetting agent, and one or more preservatives. Suitable dispersing or wetting agents and suspending agents are exemplified by those disclosed above. Additional excipients, for example, sweetening, flavoring and coloring agents, can also be present.

The GR antagonists of this invention can also be administered in the form of suppositories for rectal administration of the drug. These formulations can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

The GR antagonists of this invention can also be administered by in intranasal, intraocular, intravaginal, and intrarectal routes including suppositories, insufflation, powders and aerosol formulations (for examples of steroid inhalants, see Rohatagi (1995) *J. Clin. Pharmacol.* 35:1187–1193; Tjwa (1995) *Ann. Allergy Asthma Immunol.* 75:107–111).

The GR antagonists of the invention can be delivered by transdermally, by a topical route, formulated as applicator sticks, solutions, suspensions, emulsions, gels, creams, ointments, pastes, jellies, paints, powders, and aerosols.

The GR antagonists of the invention can also be delivered as microspheres for slow release in the body. For example, microspheres can be administered via intradermaf injection of drug (e.g., mifepristone)-containing microspheres, which slowly release subcutaneously (see Rao (1995) *J. Biomater Sci. Polym. Ed.* 7:623–645; as biodegradable and injectable gel formulations, see, e.g., Gao (1995) *Pharm. Res.* 12:857–863 (1995); or, as microspheres for oral administration, see, e.g., Eyles (1997) *J. Pharm. Pharmacol.* 49:669–674) . Both transdermal and intradermal routes afford constant delivery for weeks or months.

The GR antagonist pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5, that is combined with buffer prior to use.

In another embodiment, the GR antagonist formulations of the invention are useful for parenteral administration, such as intravenous (IV) administration or administration into a body cavity or lumen of an organ. The formulations for administration will commonly comprise a solution of the GR antagonist (e.g., mifepristone) dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of GR antagonist in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the GR antagonist formulations of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the GR antagonist into the target cells in vivo See, e.g., Al-Muhammed (1996) *J. MicroencapsuL* 13:293–306; Chonn (1995) *Curr. Opin. Biotechnol.* 6:698–708; Ostro (1989) *Am. J. Hosp. Pharm.* 46:1576–1587.

b. Determining Dosing Regimens for Glucocorticoid Receptor Antagonists

The methods of the invention treat dementia, i.e., prevent, slow the onset of, or diminish the severity of cognitive decline. The amount of CR antagonist adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the GR antagonists' rate of absorption, bioavailability, metabolism, clearance, and the like (see, e.g., Hidalgo-Aragones (1996) *J. Steroid Biochem. Mol. Biol.* 58:611–617; Groning (1996) *Pharmazie* 51:337–341; Fotherby (1996) *Contraception* 54:59–69; Johnson (1995) *J. Pharm. Sci.* 84:1144–1146; Rohatagi (1995) *Pharmazie* 50:610–613; Brophy (1983) *Eur. J Clin. Pharmacol.* 24:103–108; the latest Remington's, supra). For example, in one study, less than 0.5% of the daily dose of mifepristone was excreted in the urine; the drug bound extensively to circulating albumin (see Kawai (1989) supra). The state of the art allows the clinician to determine the dosage regimen for each individual patient, GR antagonist and disease or condition treated. As an illustrative example, the guidelines provided below for mifepristone can be used as guidance to determine the dosage regiment, i.e., dose schedule and dosage levels, of any GR antagonist administered when practicing the methods of the invention.

Single or multiple administrations of GR antagonist formulations can be administered depending on the dosage and frequency as required and tolerated by the patient. The formulations should provide a sufficient quantity of active agent, i.e., mifepristone, to effectively treat the dementia. Thus, one typical pharmaceutical formulations for oral administration of mifepristone is in a daily amount of between about 0.5 to about 20 mg per kilogram of body weight per day. In an alternative embodiment, dosages are from about 1 mg to about 4 mg per kg of body weight per patient per day are used. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable GR antagonist formulations will be known or apparent to those skilled in the art and are described in more detail in such publications as Remington's, supra. See also Nieman, In "Receptor Mediated Antisteroid Action," Agarwal, et al., eds., De Gruyter, New York (1987).

After a pharmaceutical comprising a GR. antagonist of the invention has been formulated in a acceptable carrier, it can be placed in an appropriate container and labeled for treatment of an indicated condition. For administration of GR antagonists, such labeling would include, e.g., instructions concerning the amount, frequency and method of administration. In one embodiment, the invention provides for a kit for the treatment of dementia in a human which includes a GR antagonist and instructional material teaching the indications, dosage and schedule of administration of the GR antagonist.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

The following example is offered to illustrate, but not to limit the claimed invention.

Example 1

Treating Dementia with Mifepristone

The following example details a study which demonstrates that the methods of the invention are an effective treatment for dementia.

Study Background

This study will demonstrate that a glucocorticoid receptor (GR) antagonist, mifepristone, administered in dosages of about 200 mg daily is an effective treatment to slow the cognitive decline early in the course of Alzheimer's disease.

Patient Selection

Individuals in this study are diagnosed in the early stages of Alzheimer's disease using subjective and objective criteria, including criteria as set forth by the National Institute of Neurological Diseases and Stroke (NINCDS) and the DSM-IV, as described above. All patients will give their written consent to a protocol approved by the Human Subjects Committee at Stanford University Medical Center.

Only patients with a diagnosis of dementia of the Alzheimer's type confirmed by two psychiatrists are enrolled in the study. Only patients who are relatively early in the course of the disease will be selected, i.e., only individuals whose dementia has not progressed into an advanced state will be included in the study. For example, a patient is considered to be early in the course of Alzheimer's disease if the individual can score at least about 21 on the Folstein Mini Mental Status Exam. Requiring that the subject's MMSE score be at least 21 ensures that he/she will be entered early enough in the course of their disease so that a reasonable longitudinal course can be calculated.

Patients with known endocrine disorders or any other significant medical illness are excluded. Individuals with Alzheimer's disease who carry the ApoE e4 allele are not admitted into this study. A subject whose daily use of alcohol is greater than 3 ounces or has a history of alcohol dependence will also be excluded.

Laboratory Tests

Afternoon Cortisol Test measurements will be the baseline cortisol measures for this study (taken at Day 0). Beginning one week after receiving the medication or placebo (Day 14), and each visit until the end of the study, the subject is admitted as an outpatient for blood tests and psychological and cognitive evaluation. Patients return every fourth week for the remaining four months. Cortisol levels is measured serially every half-hour from 1300 to 1600; plasma ACTH will be measured serially every hour from 1300 to 1600. In addition, blood will be taken for CBC differential and Chem 20 lab tests. These hematologic tests will be carried out before the first dose (medication or placebo) on days 0, 14, and 28, and then every four weeks until the study ends (six months total). The following schedule will be used for each visit after Day 7.

| TIME | ACTION |
|------|--------|
| 1130 | admission (outpatient status) |
| 1145 | administration of physical and cognitive symptoms checklist |
| 1200 | lunch |
| 1245 | placement of intravenous line |
| 1300–1600 | blood drawn every half-hour for cortisol |
| 1300–1600 | blood drawn every hour for ACTH |
| 1600 | receipt of mifepristone or placebo (28-day supply) |

Side effects, if any, will be carefully recorded at each visit by all research investigators who meet with the subject. Research physicians will monitor each subject during the course of the protocol and recommend appropriate action for adverse reactions.

Measuring Blood Cortisol Levels

The "Double Antibody Cortisol Kit™" (Diagnostic Products Corporation, Los Angeles, Calif.) is used to measure blood cortisol levels. This test is a competitive radioimmunoassay in which $^{125}$I-labeled cortisol competes with cortisol from an clinical sample for antibody sites, and is performed essentially according to manufacturer's instructions using reagents supplied by manufacturer. Briefly, blood is collected by venipuncture and serum separated from the cells. The samples are stored at 2 to 8° C. for up to seven days, or up to two month frozen at −20° C. Before the assay, samples are allowed to come up to room temperature (15–28° C.) by gentle swirling or inversion. Sixteen tubes in duplicate at 25 microliters of serum per tube are prepared. Cortisol concentrations is calculated from the prepared calibration tubes. Net counts equals the average CPM minus the average non-specific CPM. Cortisol concentrations for the unknowns is estimated by interpolation from the calibration curve (Dudley, et al. (1985) *Clin. Chem.* 31:1264–1271).

Dosage Regimen and Administration of Mifepristone

The glucocorticoid receptor (GR) antagonist, mifepristone, is used in this study. It is administered in dosages of 200 mg daily. Seven days after the entry into the study, patients are randomized into one of two groups.

Individuals in the first group will be given 200 mg of mifepristone daily for six months. Subjects in the second group will be given a placebo daily for six months. Both the subjects and the investigators will be blind as to which compound the patient will receive.

The mifepristone tablets are supplied by Shanghai Hua-Lian Pharmaceuticals Co., Ltd., Shanghai, China (currently the sole commercial source of mifepristone).

Assessing Treatment of Dementia

To delineate any specific cognitive deficits that are associated with hypercortisolemia in Alzheimer's disease and the ability of mifepristone to slow or abate the progess and degree of dementia of the Alzheimer's type, formal psychiatric assessment and a battery of neuro-psychological tests and assessments (including the MMSE) will be administered to all subjects. These tests and diagnostic assessments will take place at baseline (patient's entry into the study) and after the first six months, at which point the patients stop taking the drug. The battery of tests include measures of verbal and nonverbal memory; executive functions, such as abstract reasoning and problem solving; language, including both confrontation naming and word fluency; visuospatial and visuoperceptual abilities; and attention.

Results

These data demonstrate that mifepristone, in the range of about 200 mg daily, is an effective and safe treatment to decrease the rate of cognitive decline in Alzheimer's disease.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method of inhibiting progression toward dementia in a person determined to have a score of between 21 and 29 on the Folstein Mini Mental Status Exam by administration of an amount of a glucocorticoid receptor antagonist effective to treat dementia.

2. The method of claim 1, wherein the glucocorticoid receptor antagonist is administered when the person is early in the course of Alzheimer's disease as indicated by a score of between about 21 and 29 on the Folstein Mini Mental Status Exam.

3. The method of claim 1, wherein the patient suffers from multi-infarct dementia.

4. The method of claim 1, wherein the glucocorticoid receptor antagonist comprises a steroidal skeleton with at least one phenyl-containing moiety in the 11-beta position of the steroidal skeleton.

5. The method of claim 4, wherein the phenyl-containing moiety in the 11-beta position of the steroidal skeleton is a dimethylaminophenyl moiety.

6. The method of claim 4, wherein the glucocorticoid receptor antagonist comprises mifepristone.

7. The method of claim 4, wherein the glucocorticoid receptor antagonist is selected from the group consisting of RU009 and RU044.

8. The method of claim 1, wherein the glucocorticoid receptor antagonist is administered in a daily amount of between about 0.5 to about 20 mg per kilogram of body weight per day.

9. The method of claim 8, wherein the glucocorticoid receptor antagonist is administered in a daily amount of between about 1 to about 10 mg per kilogram of body weight per day.

10. The method of claim 9, wherein the glucocorticoid receptor antagonist is administered in a daily amount of between about 1 to about 4 mg per kilogram of body weight per day.

11. The method of claim 1, wherein the administration is once per day.

12. The method of claim 1, wherein the mode of administration is by a transdermal application, by a nebulized suspension, or by an aerosol spray.

13. The method of claim 1, wherein the mode of administration is oral.

14. A kit for treating a person determined to have a score of between 21 and 29 on the Folstein Mini Mental Status Exam, the kit comprising:
   a glucocorticoid receptor antagonist; and,
   an instructional material teaching the indications, dosage and schedule of administration of the glucocorticoid receptor antagonist for treating a person determined to have a score of between 21 and 29 on the Folstein Mini Mental Status Exam.

15. The kit of claim 14, wherein the instructional material indicates that the glucocorticoid receptor antagonist can be administered in a daily amount of about 0.5 to about 20 mg per kilogram of body weight per day.

16. The kit of claim 15, wherein the instructional material indicates that the glucocorticoid receptor antagonist can be administered in a daily amount of about 1 to about 10 mg per kilogram of body weight per day.

17. The kit of claim 16, wherein the instructional material indicates that the glucocorticoid receptor antagonist can be administered in a daily amount of about 1 to about 4 mg per kilogram of body weight per day.

18. The kit of claim 14, wherein the glucocorticoid receptor antagonist is mifepristone.

19. The kit of claim 14, wherein the mifepristone is in tablet form.

20. A method of inhibiting progression to dementia in a person determined to have a score of between 21 and 29 on the Folstein Mini Mental Status Exam by administration of an amount of a glucocorticoid receptor antagonist effective to treat dementia wherein the antagonist is administered in a daily amount of between 0.5 and 20 mg/kilogram of body weight per day.

* * * * *